US008428915B1

(12) United States Patent
Nipko et al.

(10) Patent No.: US 8,428,915 B1
(45) Date of Patent: Apr. 23, 2013

(54) MULTIPLE SOURCES OF DATA IN A BAYESIAN SYSTEM

(75) Inventors: Joseph C. Nipko, Burlingame, CA (US); Randi A. Paynter, San Mateo, CA (US); Robert L. Phillips, Palo Alto, CA (US); Robin L. Raffard, Berkeley, CA (US)

(73) Assignee: Nomis Solutions, Inc., San Bruno, CA (US)

( * ) Notice: Subject to any disclaimer, the term of this patent is extended or adjusted under 35 U.S.C. 154(b) by 599 days.

(21) Appl. No.: 12/317,705

(22) Filed: Dec. 23, 2008

(51) Int. Cl.
*G06F 17/10* (2006.01)
*G06F 7/60* (2006.01)

(52) U.S. Cl.
USPC ...................................... 703/2; 703/6; 706/12

(58) Field of Classification Search .................. 703/2, 6; 706/12
See application file for complete search history.

(56) References Cited

U.S. PATENT DOCUMENTS

| | | | |
|---|---|---|---|
| 6,671,661 B1 | 12/2003 | Bishop | |
| 7,047,169 B2* | 5/2006 | Pelikan et al. | 703/2 |
| 7,392,157 B1 | 6/2008 | Delurgio et al. | |
| 7,882,045 B1* | 2/2011 | Cole et al. | 706/12 |
| 2005/0086579 A1* | 4/2005 | Leitner et al. | 715/500 |
| 2006/0276999 A1* | 12/2006 | Beck et al. | 702/182 |
| 2008/0091624 A1 | 4/2008 | Krikler et al. | |
| 2008/0162371 A1* | 7/2008 | Rampell et al. | 705/80 |
| 2008/0162386 A1 | 7/2008 | Rifkin et al. | |
| 2009/0070279 A1* | 3/2009 | Rajabally | 706/12 |

OTHER PUBLICATIONS

Eric Bauer, Daphne Koller, Yoram Singer, "Update rules for parameter estimation in Bayesian networks", Proceedings of the Thirteenth Annual Conference on Uncertainty in Artificial Intelligence (UAI-97) Aug. 1-3, 1997, 11 pages.*
Gelfand et al., "Generalized Linear Models: A Bayesian View," Generalized Linear Models: A Bayesian Perspective, 2000, pp. 3-21.
Xinlei Wang, "Bayesian Variable Selection for GLM," Doctoral Dissertation, University of Texas, Austin, 2002, Chapter 1 & 2.
Agresti et al., Bayesian Inference for Categorical Date Analysis, 2005.
Chen et al., "Prior elicitation, variable selection and Bayesian computation for logistic regression," J. R. Statist. Soc. B, 1999, 61, Part 1, pp. 223-242.
Mallick et al., "Combining Information from several experiments with nonparametric priors," Biometrika, 1997, 84, 3, pp. 697-706.

* cited by examiner

*Primary Examiner* — Dwin M Craig
(74) *Attorney, Agent, or Firm* — Van Pelt, Yi & James LLP

(57) ABSTRACT

Data for a transaction is modeled by receiving a source set of data. The source set of data comprises data representing a plurality of transactions stored in a source transaction database. An estimation model for modeling data for a transaction is received. A mapping between the source set of data and a model parameter database is received. The model parameter database comprises a plurality of model parameters for the estimation model. The parameters extracted from the model parameter database and the source set of data in a Bayesian framework are combined using a parameter estimation engine to obtain an updated set of model parameters. The updated set of model parameters is stored in the model parameter database.

30 Claims, 9 Drawing Sheets

MULTIPLE SOURCES OF DATA IN A BAYESIAN SYSTEM

BACKGROUND OF THE INVENTION

Statistical modeling systems input historical or known data and output a model or decision based on the input data. For example, a statistical distribution function may be output where the exact "shape" of the function depends upon one or more parameters (e.g., the first parameter of the distribution function has a first value determined by the statistical modeling system, the second parameter has a second value, etc.). In one example, a linear model is output where the linear model is described by the function $y=\beta_0+\beta_1 x+\epsilon$ and the parameters in that example are $\beta_0$ and $\beta_1$. In general, the more information input to a statistical modeling system the better the quality of the resulting model. However, there may be a number of issues which prevent additional information from being used. For example, a set of known or historical data may be owned or managed by an entity that is unwilling to share information because of competitive reasons and/or legal reasons (e.g., the information may include sensitive personal and/or financial information). It would be desirable to develop statistical modeling systems that overcome some of these issues so that more information can be used.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
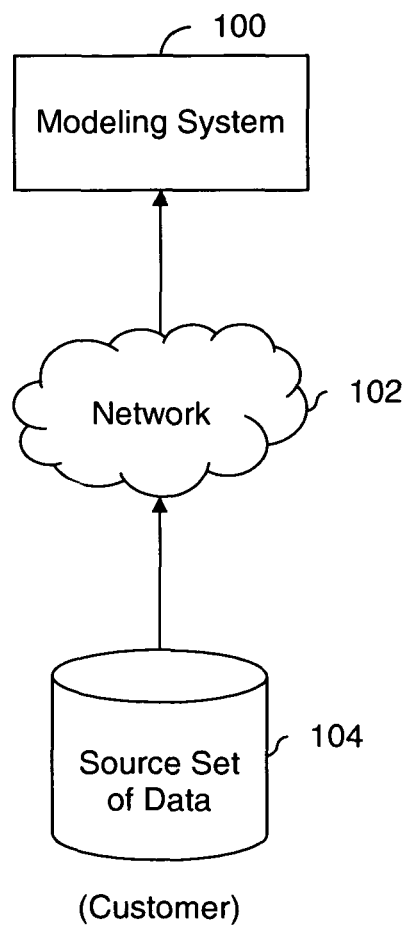
FIG. 1 is a diagram showing an example of a traditional modeling system.

FIG. 1 is a diagram showing an example of a traditional modeling system. In the example shown, source set of data 104 is a collection of known or historical data. Source set of data 104 is owned by or managed by an entity for which the statistical modeling (performed by modeling system 100) is being performed. In some cases, modeling system 100 is owned and/or managed by some other entity, such as a company that specializes in modeling.

Data from source set of data 104 is sent or otherwise accessed by modeling system 100 via network 102. In various embodiments, a network includes a variety of networking devices and/or technologies including (but not limited to) wired/wireless communication, Internet related protocols, etc.

In one example, source set of data 104 is associated with a bank and system 100 is associated with a financial services company hired by the bank to determine prices for the bank's products (e.g., rates on loans offered by the bank). In a closed loop system, the bank sets its prices (or some other adjustable value) based on the decision or estimate made by system 100, the market response to the new price is observed (e.g., whether or not consumers are taking loans with the new rates), and this information is fed back into source data set 104.

In another example, source set of data 104 contains data related to a medical research or trial. For example, a medical study may focus on which of two similar drugs is better for treating a particular disease and source set of data 104 includes the medical history of a study group (including prescribed drugs, dosages, how long a particular drug was prescribed for, etc.). In that application, modeling system 100 may access the stored medical information in source set of data 104 and generate models of the response or efficacy of the medicine.

In general, any data may be used and operated on using the techniques disclosed herein. Although certain specific applications or types of data are disclosed herein (e.g., financial data), the techniques disclosed herein are not necessarily limited to those types of data or applications.

In general, when generating or outputting a model or estimate, it is better to have more information. In the example shown, a decision is made based on information owned or managed by one particular entity, such as a single bank or a single group of medical study participants. Other information may exist (e.g., information owned by another bank or another group of medical study participants) but is not used in the system of FIG. 1. The following system shows an embodiment of a Bayesian system that uses multiple sources of data.

Figure 2A:
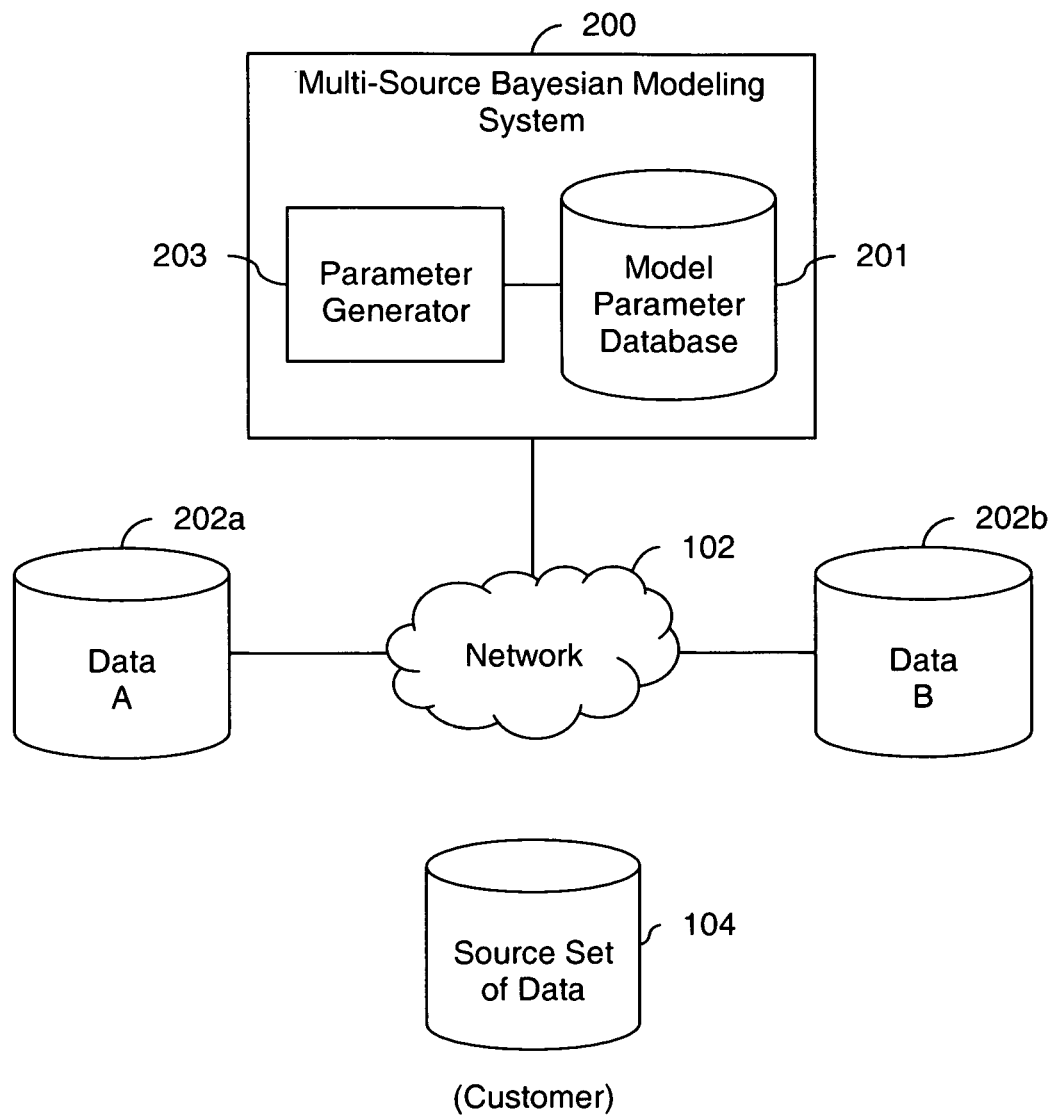
FIG. 2A is a diagram showing an embodiment of a multi-source Bayesian system at a first point in time.

FIG. 2A is a diagram showing an embodiment of a multi-source Bayesian system at a first point in time. In the example shown, multi-source Bayesian modeling system 200 includes parameter generator 203 and model parameter database 201. Parameter generator 203 is used to generate parameters based on known data. These parameters generated by generator 203 are then stored in database 201. When a model is desired, the stored parameters in model parameter database 201 are used to generate the model.

In the example shown, data A (202a) is owned or managed by a first entity (e.g., a first bank or a first researcher), data B (202b) is owned or managed by a second entity, and source set of data 104 is owned or managed by a third entity. This is merely one example. In another embodiment, data A and B (202a and 202b) are owned by the same entity and source set of data 104 is owned by some other entity. In some embodiments, a source set of data (e.g., 104) includes the same or similar types of information as other groups of data (e.g., data A and B 202a and 202b) and/or have the same types or form of data (e.g., records of individual events or transactions).

As used herein, a source set of data refers specifically to data that is owned or managed by an entity for which a model is being generated (e.g., a customer in this figure). For the example of FIG. 2A, a model is generated for the entity associated with source set of data 104. If a model were being generated for some other entity, then data 104 would be referred to simply as "data" and not a "source set of data".

In general, a given source set of data i can be expressed as $S_i(n, \vec{y}, X)$ where n is the number of observations for that particular source set of data, $\vec{y}$ is a vector of responses, and X is a n by k matrix of variables. The vector $\vec{y}$ represents the outcomes of the quantity being modeled and its values are known or historic values of y. The matrix X includes other information associated with or pertaining to each particular response for a given observation. For example, if the vector $\vec{y}$ is whether or not a customer accepts an offered loan, the matrix X may include city and state where the applicant lives, income, marital status, age, FICO score, loan amount, terms of loan, etc. If high blood pressure medication is being modeled or estimated, then the vector $\vec{y}$ may be blood pressures of study participants and the matrix X includes gender, age, whether the person smokes, etc. In some embodiments, data A and B (202a and 202b) can be expressed using the same general function.

In this example, parameter generator 203 accesses data A and B (202a and 202b, respectively) via network 102. Using this information, parameters are generated by generator 203 and are passed to model parameter database 201 where they are stored. In various embodiments, the particular parameters generated depend upon the particular model used by the system and assumed distribution of the response or error. For example, in some configurations a linear model (i.e., $y=\beta_0+\beta_1 x+\epsilon$ is used and the parameters $\beta_0$ and $\beta_1$ are generated or otherwise obtained from data A and B when the error distribution is Gaussian. In some other embodiments, a different model is used which corresponds to a different set of parameters. For example, suppose an exponential model (i.e. $y=\exp(\alpha_0+\alpha_1 x)+\epsilon$) is used where the y are assumed to follow a Poisson distribution. In such embodiments, the parameters $\alpha_0$ and $\alpha_1$ are obtained for data A and B (202a and 202b) and are stored in model parameter database 201.

In some embodiments, two different sets of parameters are generated and stored for two different sets of data. In other words, it is not necessary for the same, homogenous set of parameters to be used for all data that is processed. For example, data A (202a) may be modeled using a first model having a first set of parameters (e.g., $\beta_0$ and $\beta_1$). Values for that first set of parameters are generated by generator 203 and are stored in database 201. In some embodiments, data B (202b) uses a different model and values for a second set of parameters (e.g., $\alpha_0$ and $\alpha_1$) are generated and stored. In some embodiments, the same set of parameters is used for data A and B (202a and 202b). For example, a first set of parameter values are generated and stored for data A (e.g., $\beta_{0A}$ and $\beta_{1A}$) and a second set of parameter values are generated and stored for data B (e.g., $\beta_{0B}$ and $\beta_{1B}$). In some embodiments, when processing a group of data, a user specifies to parameter generator 203 which model (and thus, which parameters) to generate for a given group of data. In some embodiments the model and corresponding parameters are automatically selected.

In various embodiments, model parameter database 201 generates, stores, and/or otherwise manages parameters in a variety of ways. Some examples are described herein but are not intended to be limiting.

In some applications, the number of parameters generated by generator 203 and stored in database 201 is much smaller than the number of samples in an original or "raw" data set. In some cases, data A and/or B (202a and 202b) includes hundreds of thousands or millions of records whereas database 201 includes hundreds or thousands of parameters. In some cases, the records describe an individual event or transaction, for example a car loan. The record may include information over the lifetime of the event, for example beginning from an application process (e.g., applicant's credit score, down payment, etc.) to how the loan was concluded (e.g., paid off by borrower, defaulted, etc.). If both data A and data B (202a and 202b) are modeled using a linear model (i.e., $y=\beta_0+\beta_1 x+\epsilon$) then only two parameters are stored.

Figure 2B:
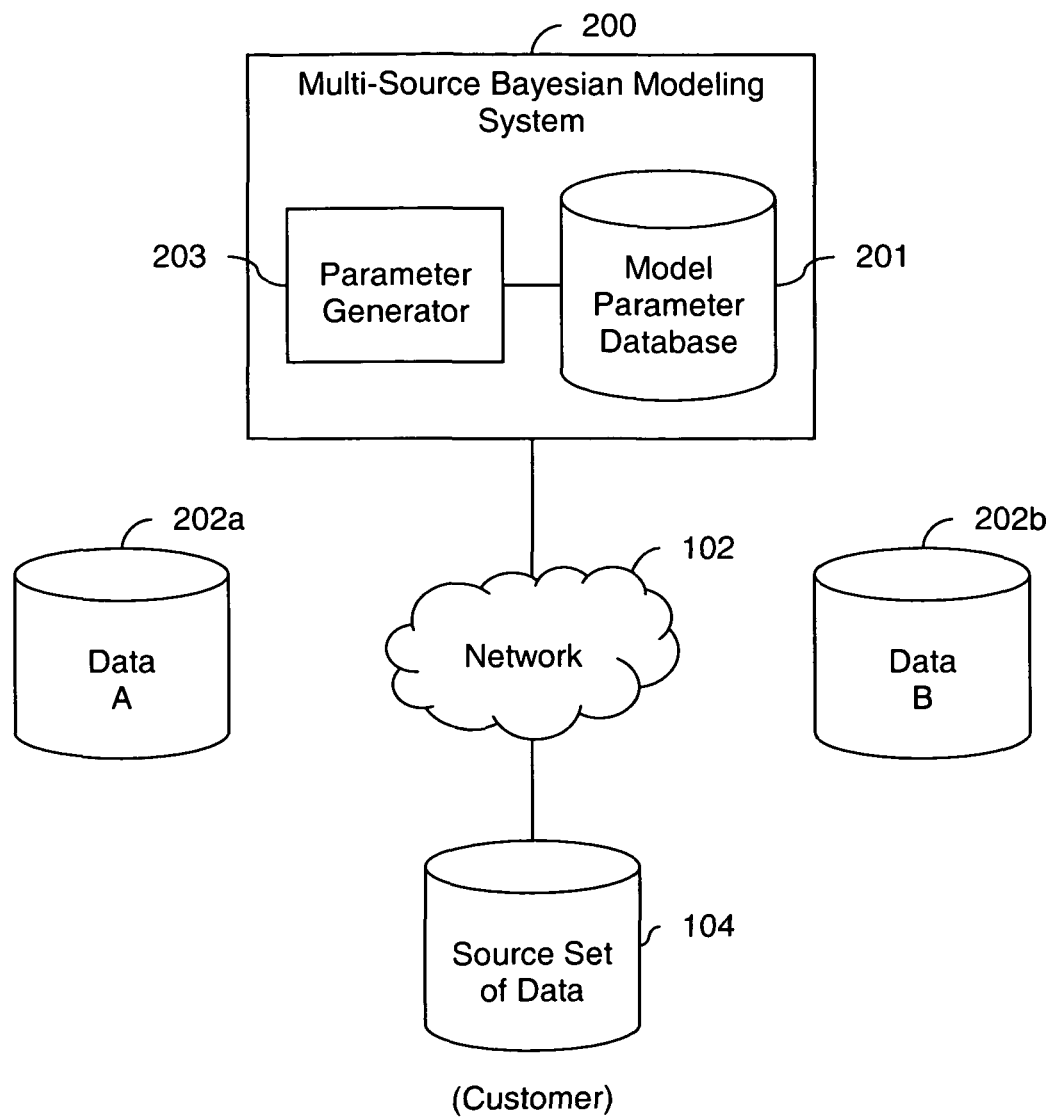
FIG. 2B shows an embodiment of a multi-source Bayesian system at a second point in time.

FIG. 2B shows an embodiment of a multi-source Bayesian system at a second point in time. FIG. 2B shows the system of FIG. 2A at a later point in time. In this example, parameters have been generated using data A and B and are stored in model parameter database 201. Data A and B (202a and 202b) in this particular example are no longer available via network 102 and the original data can no longer be accessed.

Data from a source set of data (104) is accessed by multi-source Bayesian modeling system 200 via network 102. Using the source set of data (104) and parameters in model parameter database (201) a decision is made or a model is estimated by multi-source Bayesian modeling system 200. In some embodiments, this is performed by first having parameter generator 203 generate parameter values using source set of data 104 (e.g., by mapping variables in source set o data 104 to corresponding parameters using a map) and then storing the parameter(s) in database 201. Using the information stored in database 201 (e.g., including the parameter(s) generated from data A (202a), data B (202b), and source set of data (104)), an estimate or model is generated for the customer. Later, the parameters generated and stored in database 201 can be used for another customer if desired.

In various financial embodiments, a model or other decision made by multi-source Bayesian modeling system 200 is customized or generalized. A customized decision is one that is made for a particular person, entity, and/or transaction. For example, if a person wants a line of credit using their home as collateral, a personalized decision is one that is made only for that person and typically the terms of the offer (e.g., for a line of credit) are not known a-priori. In contrast, a generalized price is determined ahead of time for one or more groups. For example, people may be divided into one or more groups based on income and/or credit score. For each group, the people in a given group are offered the same price or terms.

Returning to FIG. 2B, suppose the source set of data (104) is associated with a bank and the bank hires a financial services company to determine prices for the bank's products. Multi-source Bayesian modeling system 200 determines optimal parameters (or makes some other decision) based on information obtained from that bank, as well as parameters from other sources or entities (e.g., generated using data A and B and stored in model parameter database 201). Compared to the system shown in FIG. 1, information from multiple sources (and thus more information) is used in making a decision or model which in general improves the performance of the system.

One benefit to the system shown in FIGS. 2A and 2B is that the system can estimate model parameters or make a decision based on multiple sources of data even when the original data (e.g., data 202a and 202b) is no longer available. This occurs in real-life for a variety of reasons. In one example, a data set includes patient records or patient information. The owner of the patient information (e.g., a hospital) may be unwilling to provided access to the information for an unlimited period of time because of patient confidentiality laws or liability issues. In another example, there is a contractual agreement to only have access to information for a certain amount of time or until a task is completed. Multi-source Bayesian modeling system 200 overcomes these issues since only parameters are stored in model parameter database (which are anonymous and do not include identifying information such as names) and access to data 202a and 202b can be cut off after the parameters have been obtained and stored. Also, since parameters are different from the "raw" or original data, they can be kept and used later even if there is a contractual obligation to return or delete the "raw" or original data. That is, the parameters are the property of the entity that generated the parameters, not the entity that owns or manages the raw data itself.

Multi-source Bayesian modeling system 200 is also different from a modeling system in which data from multiple sources is crudely combined together (e.g., source set of data (104) ∪ data A (202a) ∪ data B (202b)). Data A and B (202a and 202b) may contain millions of transactions or other pieces of information. The parameters determined and stored in model parameter database 201 range (in some embodiments) from one or two parameters to hundreds of parameters. Much less information needs to be stored and processed. In contrast, data which is merely combined together would be quite large, making it difficult to store and manage. Also, data sets do not always have corresponding or similar data and crudely combining data together provides little or no instruction on how to handle situations in which there are different types of data, one set has no information but another set does, etc. For example, if information from two different medical studies are combined, different techniques may have been used or different patient information may have been recorded (e.g., one study asked a patient's ethnic background and the other did not record this information). Multi-source Bayesian modeling system 200 includes techniques to address this issue of processing data from multiple sources. In some embodiments described in further detail below, a mapping is used to correlate or indicate which pieces of data in the source set of data (104) correspond to which parameter(s) (if any) stored in model parameter database 201. In some embodiments described herein, parameters are used (as opposed to the "raw" data such as data 202a and 202b) and therefore a mapping (or other technique) is between a source set of data (104) and parameters in database 201, not between the source set of data (104) and data A and B (202a and 202b).

The examples shown in FIGS. 2A and 2B are merely illustrative of the techniques which are sought to be patented. In some cases, data 202a, 202b, and 104 may be connected to network 102 at the same time. In some embodiments, the ordering of processing is reversed. For example, in some configurations the source set of data 104 is processed first, and then data 202a and 202b. Any number or amount of data can be processed. For example, additional sets of data owned or managed by some other entity (or alternatively, source data owned or managed by the entity for which the modeling is being performed) can be processed after the state shown in FIG. 2B.

Figure 3:
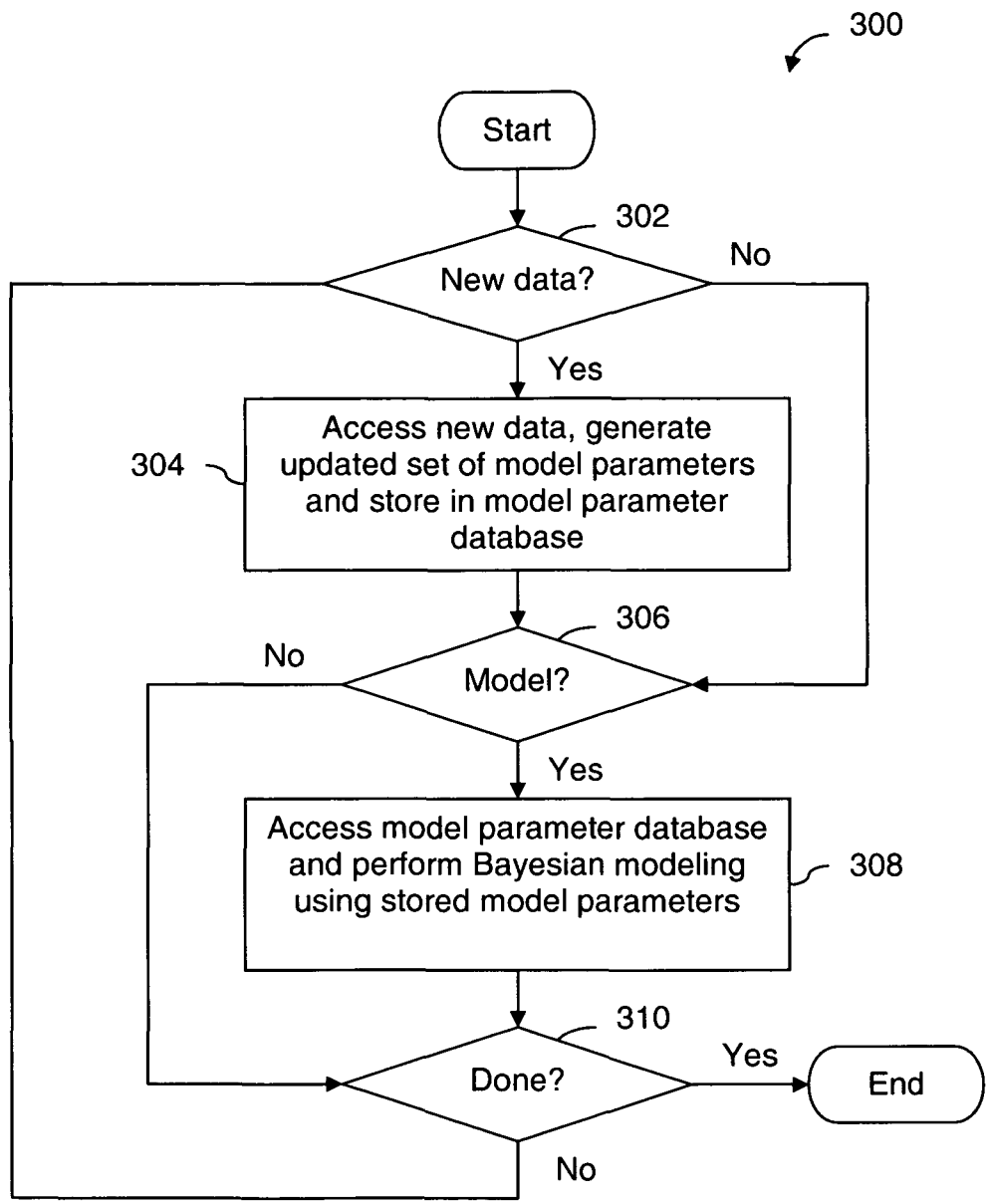
FIG. 3 is a flowchart illustrating an embodiment of a process for managing a model parameter database and performing Bayesian modeling using a model parameter database.

FIG. 3 is a flowchart illustrating an embodiment of a process for managing a model parameter database and performing Bayesian modeling using a model parameter database. In the example shown, information from multiple sources is used, for example from a plurality of financial institutions, medical studies, etc. In some embodiments, multi-source Bayesian modeling system 200 shown in FIGS. 2A and 2B is managed using example process 300.

At 302 it is determined whether new data is available. For example, in FIG. 2A new data 202a and 202b become available. If new data is available, the new data is accessed and an updated set of model parameters is generated and is stored in a model parameter database at 304. In FIG. 2A for example, data A and B (202a and 202b) are accessed, an updated set of model parameters is generated by parameter generator 203 and is then stored in model parameter database 201. In some embodiments, generating and storing an updated set of model parameters includes (re)generating an entire set of information and overwriting old information stored in the database. Alternatively, in some other embodiments, information is generated and stored in the database without writing over previously generated and previously stored information.

After updating at 304 (or, if there is no new data available, at 306) it is decided whether to perform modeling. If so, the model parameter database is accessed and Bayesian modeling using stored model parameters is performed at 308. For example, the parameters stored in database 201 are accessed and are used in Bayesian modeling. In some embodiments, some other information is used in performing Bayesian modeling (e.g., source set of data 104 associated with the customer in FIG. 2B).

After performing modeling at 308 or if no modeling was performed, at 310 it is determined whether the process is over. For example, a model parameter database may be shut down. If so, the process ends. Otherwise, it is determined at 302 whether new data is available.

Figure 4:
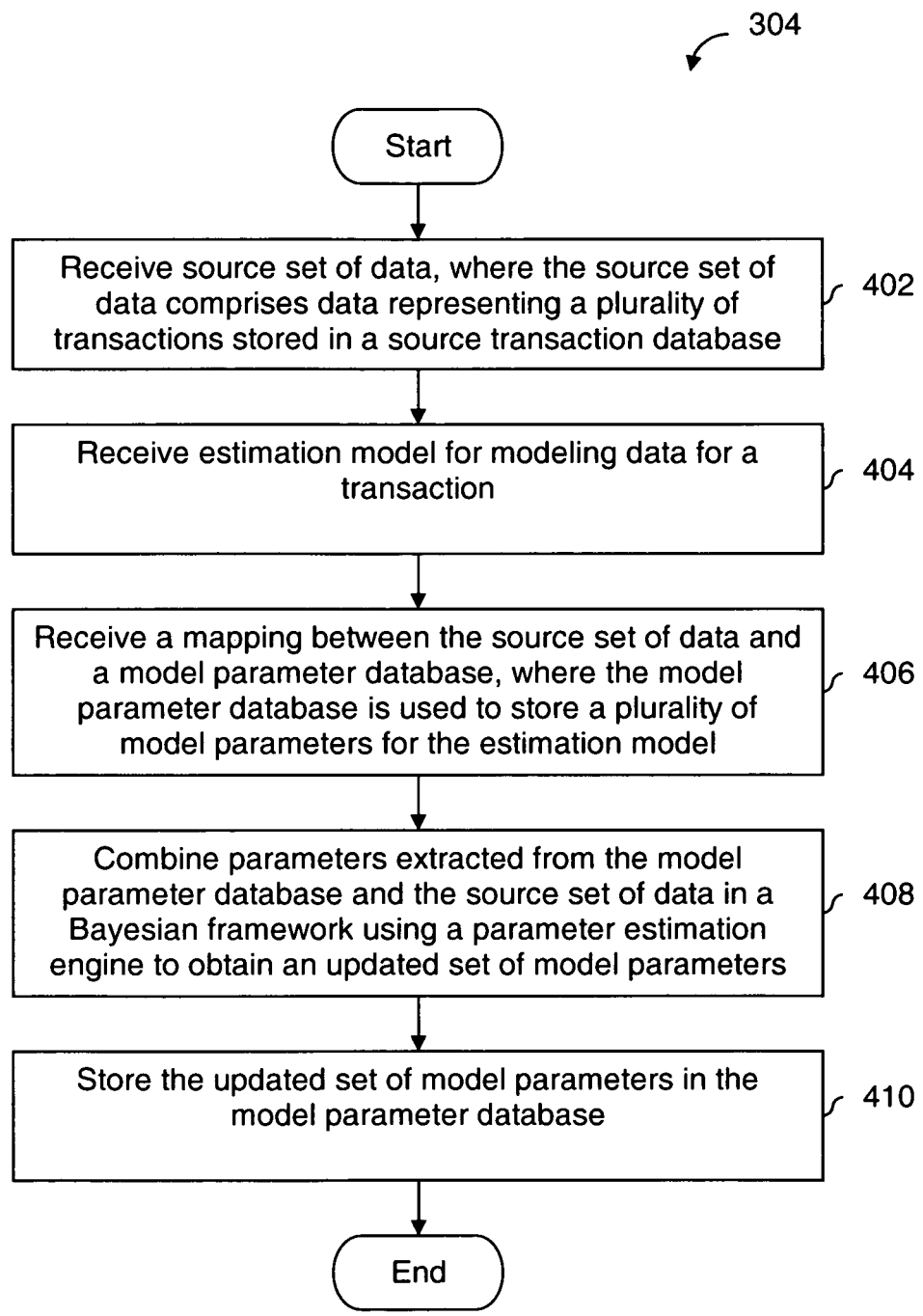
FIG. 4 is a flowchart illustrating an embodiment of a process for updating a model parameter database.

FIG. 4 is a flowchart illustrating an embodiment of a process for updating a model parameter database. In some embodiments, step 304 of FIG. 3 is implemented as shown. In some embodiments, a model parameter database is updated in some other manner.

At 402, a source set of data is received where the source set of data comprises data representing a plurality of transactions stored in a source transaction database. For example, in FIG. 2B, source set of data 104 is received.

At 404, an estimation model is received for modeling data for a transaction. For example, a multi-source Bayesian modeling system may be capable of generating and storing different parameters for different types of models (e.g., linear model, hazard model, etc.) and step 404 is used to specify which type of model (and thus, which parameters are to be used) for the source set of data received at 402. In some embodiments, the estimation model is received from or otherwise specified by a user (e.g., a modeling expert). In some embodiments, the estimation model is determined or selected automatically For example, in modeling loan take-up probability for unsecured personal loans an example of a pre-defined model could have the form Probability(Take-up)=Logit($\beta_0+\beta_1$ Loan Rate+$\beta_2$ Probability of Default).

At 406, a mapping between the source set of data and a model parameter database is received, where the model parameter database is used to store a plurality of model parameters for the estimation model. One embodiment of a mapping is described in further detail below.

At 408, parameters extracted from the model parameter database and the source set of data are combined in a Bayesian framework using a parameter estimation engine to obtain an updated set of model parameters. For example, this includes using the mapping obtained at 406 and the source set of data obtained at 402.

An updated set of model parameters are stored in the model parameter database at 410. For example, parameter generator 203 outputs an updated set of parameters which are stored in model parameter database 201.

Figure 5:
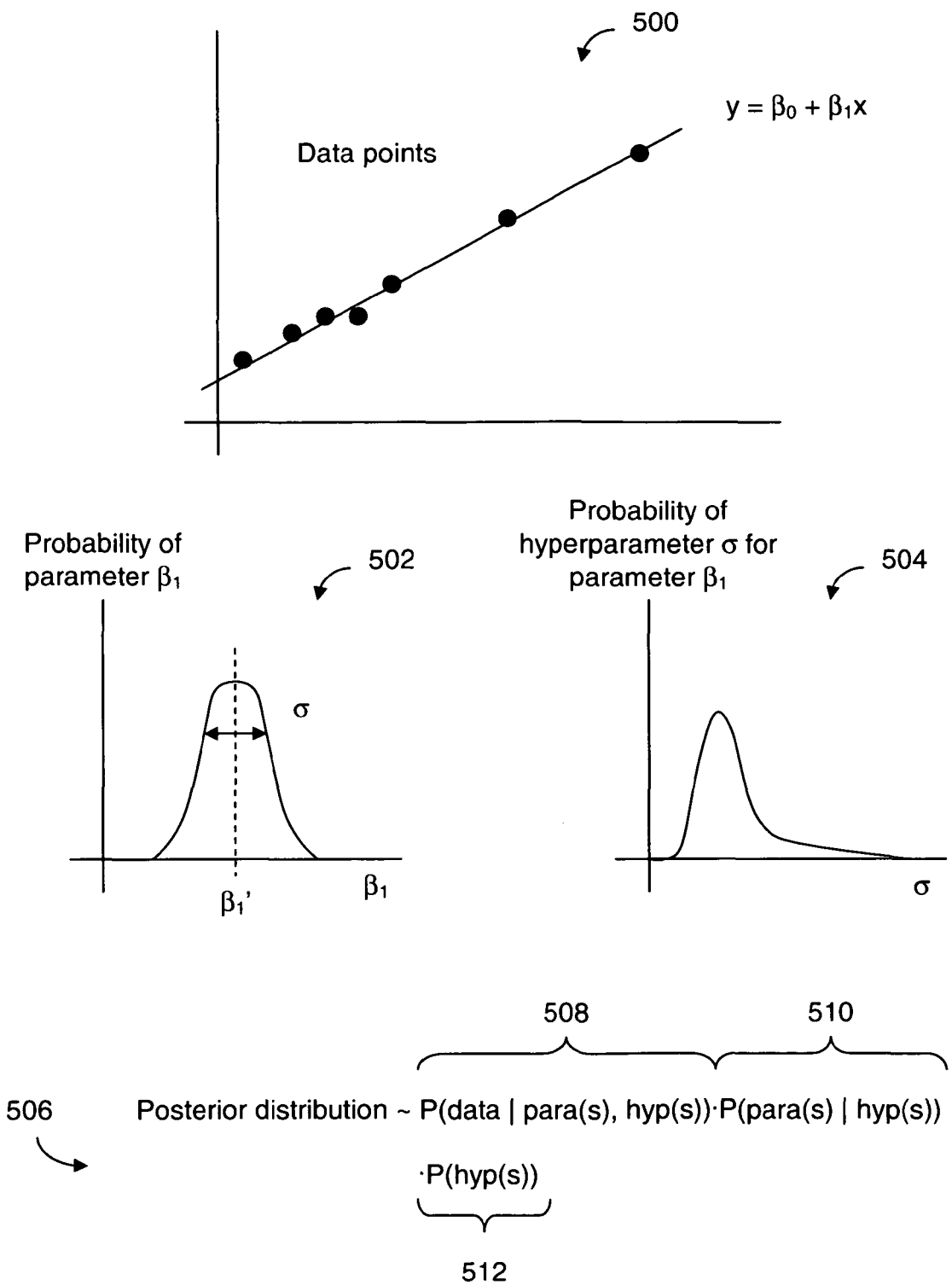
FIG. 5 is a diagram showing a posterior distribution and associated graphs.

FIG. 5 is a diagram showing a posterior distribution and associated graphs. In the example shown, a linear function $y=\beta_0+\beta_1 x+\epsilon$ is output by a multi-source Bayesian modeling system. For this particular model (i.e., a linear model) the values of the parameters $\beta_0$ and $\beta_1$ are determined. Graph 500 shows an example line and corresponding data points from which the line is determined.

Graph 502 shows a distribution for the parameter $\beta_1$. The x-coordinate of graph 502 shows possible values of $\beta_1$ and the y-coordinate shows the probability of a given value of $\beta_1$. $\beta_1'$ is the mean of the distribution shown in graph 502 and the value of $\beta_1$ selected by a multi-source Bayesian system will be in the range of $\beta_1'$.

The particular distribution obtained or realized for $\beta_1$ will depend on the hyperparameters of the distribution. In this particular example, the hyperparameter $\sigma$ corresponds to the variance of the distribution shown in graph 502. Some other models or parameters may depend upon different hyperparameters. Graph 504 shows a distribution for the hyperparameter $\sigma$. The x-coordinate of graph 504 shows the possible values of $\sigma$ and the y-coordinate shows the probability for a given value. The distribution of $\sigma$ shown in graph 504 affects the distribution of $\beta_1$ shown in graph 506 which in turn affects the value of $\beta_1$ output by a multi-source Bayesian modeler.

Equation 506 shows a posterior distribution which comprises of two conditional probabilities which are multiplied together. Conditional probability 508 is the probability of data (such as the data points shown in graph 500), given parameter(s) (such as $\beta_0$ and $\beta_1$) and hyperparameter(s) (such as $\sigma$). Conditional probability 510 is the probability of the parameters given the hyperparameter(s). Probability 512 is the probability of a hyperparameter. Other Bayesian systems which do not use multiple sources of data typically "freeze" conditional probability 510 and/or probability 512. For example, they may pick a value for a hyperparameter (such as $\sigma$) and use that value without updating it. One problem with this is that a hyperparameter (and thus the value of a corresponding parameter determined by a system) may change over time. For example, in the case of a medical study of an antibiotic, the antibiotic may become less effective over time as the organisms evolve and develop a resistance to the drug. Freezing conditional probability 510 may prevent a Bayesian system from having as accurate an estimate as would be desired. In contrast, a multi-source Bayesian system does not freeze conditional probability 510.

As used herein, a hyperparameter controls or otherwise affects the particular shape or realization of a given distribution. A distribution has one or more hyperparameters associated with it and one distribution may not necessarily have the same number or type of hyperparameters as another distribution.

Parameters are used to propose a mathematical model for an observed phenomena in terms of observed effects. A hyperparameter is used to formulate the distribution of likely values for a parameter of a model. For example, if it is assumed the values of a model parameter are randomly distributed about a mean value, then parameter values would follow a Gaussian distribution. In order to fully characterize a Gaussian distribution both the mean and variance would be required. The variance in this case would be a hyperparameter for any model parameter that follows a Gaussian distribution.

Figure 6:
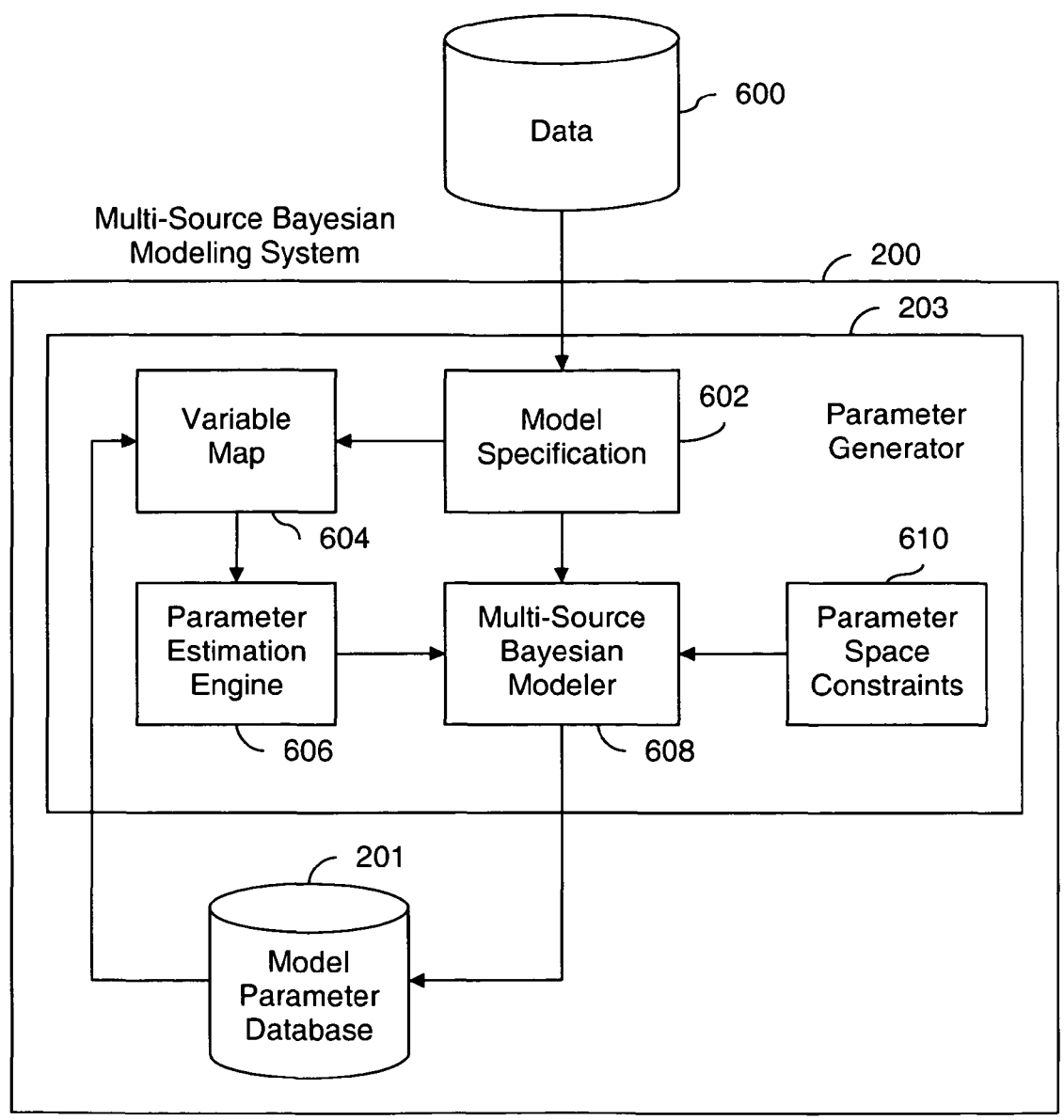
FIG. 6 is a diagram showing an embodiment of a parameter generator.

FIG. 6 is a diagram showing an embodiment of a parameter generator. In some embodiments, parameter generator 203 of FIGS. 2A and 2B is implemented as shown. In some embodiments, a parameter generator is implemented in some other manner.

Parameter generator 203 in this embodiment includes model specification 602. In this system, data 600 is accessed or otherwise passed to model specification 602 (e.g., via a network) where one or more models are specified for a particular effect being modeled (e.g., conversion, number of loans accepted in particular time period, utilization of a line of credit, etc.) and model specification 602 specifies a model to use. In one example, block 602 may specify to use a linear model having corresponding parameters. Data 600 in this example can be any data. For example, at the point in time shown in FIG. 2A, data 600 corresponds to data A and/or data B (202a and/or 202b). At the point in time shown in FIG. 2B, data 600 corresponds to source set of data 104.

The historical data included in data 600 is passed via model specification 602 to map 604. As used herein, a map is a mapping which describes which variables in the samples or pieces of historical data map to which parameters. For example, in the case of a medical study, the variables may be age, gender, smoker/non-smoker, number of hours person works out in a week, etc. An example of a map is described in further detail below.

Based on which parameters are being mapped to (i.e., known from map 604), stored values for those parameters are accessed from model parameter database 201 and passed to parameter estimation engine 606 via map 604. In this example, parameter estimation engine 606 outputs a single value or function for a given parameter from multiple, stored values or functions. For example, a plurality of stored values or functions for the parameter $\lambda$ may be passed to parameter estimation engine 606 and a single value or function for the parameter $\lambda$ is output. In some embodiments, there are multiple parameters and a single one is output by parameter estimation engine 606 for each parameter. The end parameter will be a weighted average based on the hyperparameter(s) of the assumed distributions.

The parameter(s) output by parameter estimation engine 606 are passed to multi-source Bayesian modeler 608, which also receives information from model specification 602. In this embodiment, multi-source Bayesian modeler is configured to be able to operate or otherwise process a variety of models and so model specification 602 identifies which model to use. Model specification 602 also passes information from data 600 to multi-source Bayesian modeler 608. For example, if FIG. 6 corresponded to the system shown in FIG. 2B, multi-source Bayesian modeler 608 would use information from data A and B (stored in model parameter database 201 and passed to modeler 608 via map 604 and parameter estimation engine 606) and information from source set of data 104 (i.e., data 600 and passed to modeler 608 via model specification 602).

In this example, multi-source Bayesian modeler 608 also inputs constraints from parameter space constraints 610. Multi-source Bayesian modeler 608 uses these constraints (if any) to alter the probability distribution of the parameters in a way that would not otherwise come about based solely on the data passed to modeler 608. Some examples of constraints include trending, shifting, rounding, applying a floor or ceiling value, etc. In some embodiments, parameter space constraints 610 includes expert knowledge. For example, there may be some knowledge an expert user has about the system and/or what the model that is output should resemble and this expert knowledge is input to the system using parameter space constraints 610. In some embodiments, parameter space constraints 610 is optional and is not included in a parameter generator.

Figure 7:
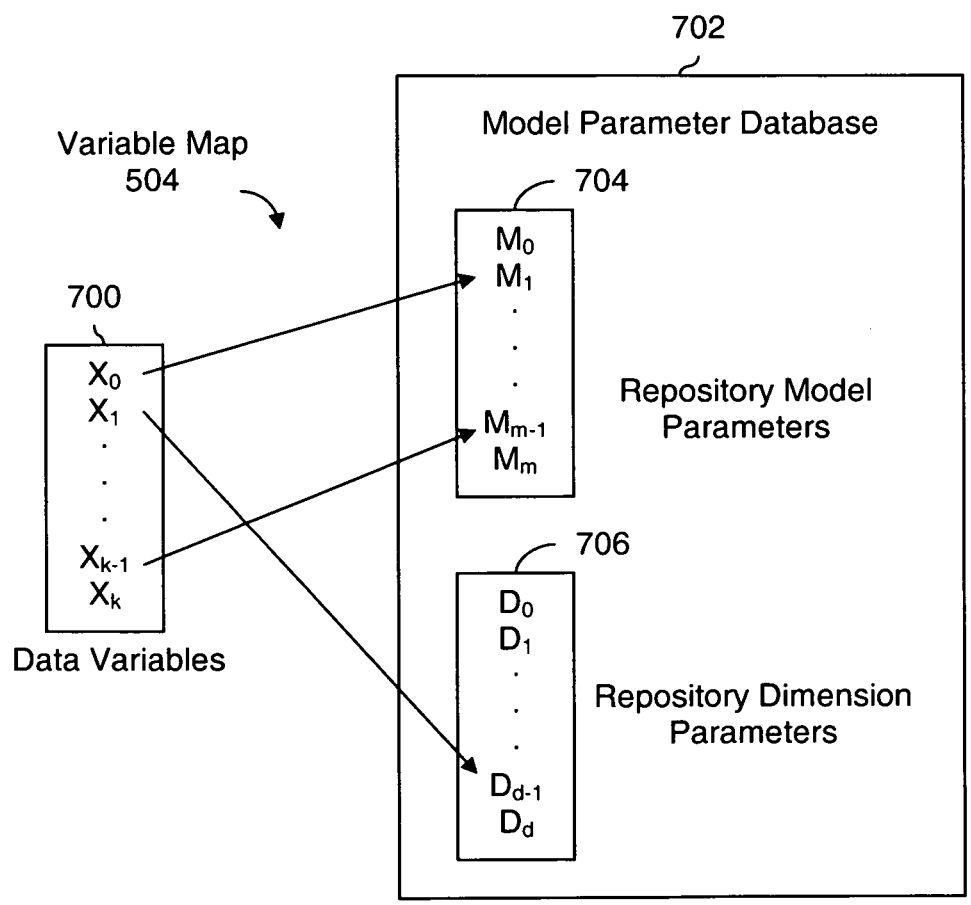
FIG. 7 is a diagram showing an embodiment of a map between variables in data and parameters stored in a model parameter database.

FIG. 7 is a diagram showing an embodiment of a map between variables in data and parameters stored in a model parameter database. In some embodiments, variable map 604 is implemented as shown.

As described above, "raw" data in general can be expressed as $S_i(n, \vec{y}, X)$ where n is the number of observations for that particular source set of data, $\vec{y}$ is a vector of responses, and X which is a n by k matrix of variables. The arrows between data variables 700 and model parameter database 702 (which include repository model parameters 704 and repository dimension parameters 706) comprise map 604. In this example, variable $X_0$ maps to $M_1$ of repository model parameters 704, variable $X_1$ maps to $D_{d-1}$ of repository dimension parameters 706, and variable $X_{k-1}$ maps to $K_{m-1}$ of repository model parameters 704.

For those variables that map to a parameter in repository model parameters 704, those parameters are used in parameter estimation and multi-source Bayesian modeling. For example, referring to the examples of FIGS. 6 and 7, repository parameters models $M_1$ and $M_{m-1}$ would be output by map 604 and passed to parameter estimation engine 606.

Some variables, such as variable $X_k$ may not map to anything. In such cases, this means there is currently no parameter stored in the model parameter database which maps to that variable. In some embodiments, a new parameter is created and stored. In some embodiments, information associated with that variable is not used.

Some variables, such as variable $X_1$, map to a dimension in repository dimension parameters 706. Dimensions are typically used to segment data into like groups in terms of response. For example, in modeling the number of vehicle loans originated by a particular financial institution, the data would typically be segmented along dimensions of vehicle age. As another example, age and gender would be typical dimensions in a medical study of drug effectiveness.

Figure 8:
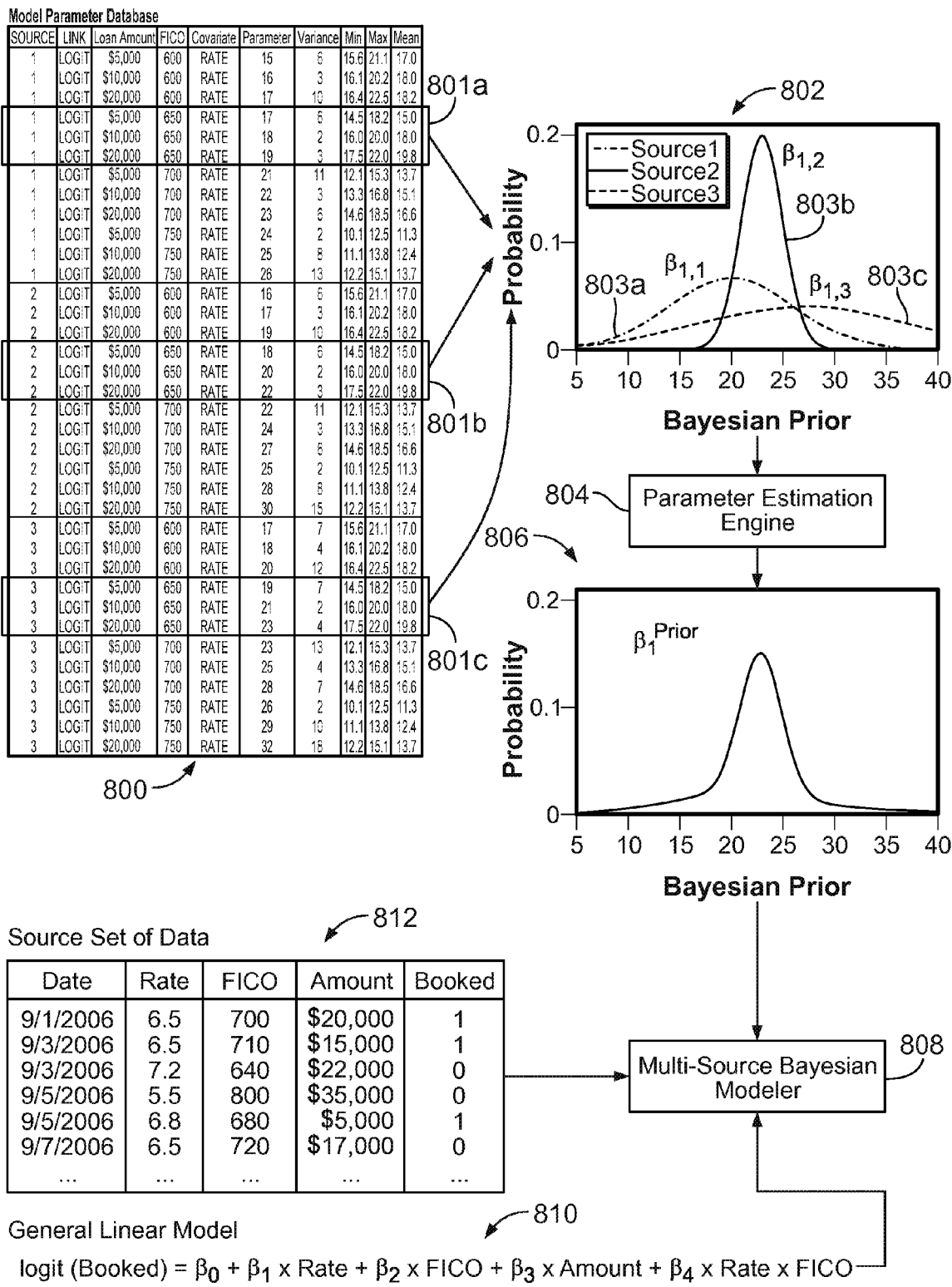
FIG. 8 is a diagram showing an embodiment of a multi-source Bayesian system that processes financial data.

FIG. 8 is a diagram showing an embodiment of a multi-source Bayesian system that processes financial data. In the example shown, model parameter database 800 and source set of data 812 include financial data. The columns in model parameter database 800 include a source (e.g., source 1 corresponds to loans from one bank, source 2 corresponds to loans from a second bank, and source 3 corresponds to loans from third bank), loan amount, FICO score, covariate, parameter, variance of the parameter, and min, max, and mean of the covariate.

Three groups of data 801a-801c are accessed from model parameter database 800 and are shown in graph 802. Data 801a-801c correspond to sources 1-3, respectively and are shown as curves 803a-803c in graph 802. In this particular example, data 801a-801c include loan information for people with FICO scores of 650 and are shown as parameters $\beta_{1,1}$, $\beta_{1,2}$ and $\beta_{1,3}$, respectively.

Data 801a-801c is passed to parameter estimation engine 804 which outputs a single parameter $\beta_1^{prior}$ which is shown in graph 806. This is passed to multi-source Bayesian modeler 808. Although this model used in this particular example uses additional parameters (e.g., $\beta_0$ and $\beta_2$-$\beta_4$), for clarity, only parameter $\beta_1$ is shown.

In some embodiments, the particular data or parameters that are obtained from model parameter database 800 depends upon which model is selected to be used. For example, in the system of FIG. 6, model specification 602 specifies which model to use (and thus, which parameters are applicable).

In addition to the parameter $\beta_1^{prior}$ which is output by parameter estimation engine 804, multi-source Bayesian modeler 808 also receives information from source set of data 812 and general linear model 810. In some embodiments, multiple models are available and some entity (e.g., model specification 602 in the embodiment of FIG. 6) selects or specifies the model to be used and passes it to multi-source Bayesian modeler 808. In this particular example, a linear model is used and the model is associated with whether or not a loan is booked (i.e., accepted by a customer in the event a loan is offered) and is $\beta_0+\beta_2\times\text{Rate}+\beta_2\times\text{FICO}+\beta_3\times\text{Amount}+\beta_4\times\text{Rate}\times\text{FICO}$. Multi-source Bayesian modeler also inputs source set of data 812. In some embodiments, the entity that owns or manages source set of data 812 is some other entity besides sources 1-3. In some embodiments, modeling is being performed for the entity that owns or manages source set of data 812.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   receiving a source set of data, wherein the source set of data comprises data representing a plurality of transactions stored in a source transaction database;
   receiving an estimation model for modeling data for a transaction;
   receiving a mapping between the source set of data and a model parameter database, wherein the model parameter database comprises a plurality of model parameters for the estimation model;
   using a processor to generate an updated set of model parameters, including by:
      determining which model parameters in the model parameter database are mapped to by the mapping; and
      updating those model parameters in the model parameter database which are mapped to by the mapping, without updating those model parameters in the model parameter database which are not mapped to by the mapping; and
   storing the updated set of model parameters in the model parameter database.

2. The method of claim 1 further comprising:
   receiving one or more parameter space constraints; and
   combining the parameters includes using the parameter space constraints.

3. The method of claim 1, wherein the estimation model is selected from a group of a risk model, a conversion model, a default model, and a price sensitivity model.

4. The method of claim 1, wherein the mapping is based on a probabilistic similarity of database attributes and source data attributes.

5. The method of claim 1 further comprising extracting relevant information from the model parameter database using a distance metric function that produces a trade-off of information similarity and time weighting.

6. The method of claim 1 further comprising receiving one or more parameter space constraints, wherein combining the parameters includes using the parameter space constraints.

7. The method of claim 1 further comprising outputting a model by accessing the updated set of model parameters stored in the model parameter database.

8. The method of claim 7, wherein outputting a model includes using a posterior probability.

9. The method of claim 1, wherein the source set of data comprises data representing a plurality of prior loan transactions, including a loan amount, a credit rating score, and an interest rate for a loan.

10. The method of claim 1, wherein using the processor to generate further includes: generating, for at least one model parameter in the updated set of model parameters, a distribution function that includes (1) a range of values for the at least one model parameter and (2) a range of probabilities corresponding to the range of values.

11. The method of claim 10, wherein generating the distribution function includes using a distribution function associated with a hyperparameter, wherein:
the distribution function associated with the hyperparameter includes (1) a range of values for the hyperparameter and (2) a range of probabilities corresponding to the range of values for the hyperparameter; and
the distribution function associated with the hyperparameter affects the distribution function generated for the at least one model parameter.

12. The method of claim 10, wherein the distribution function is a combined distribution function and generating the combined distribution function includes: combining (1) a first distribution function, for the at least one model parameter, generated from a first set of data and (2) a second distribution function, for the at least one model parameter, generated from a second set of data which does not overlap with the first set of data.

13. The method of claim 12, wherein at least one of the following is inaccessible when the combined distribution function is generated: the first set of data or the second set of data.

14. A system, comprising:
an interface configured to:
receive a source set of data, wherein the source set of data comprises data representing a plurality of transactions stored in a source transaction database;
receive an estimation model for modeling data for a transaction; and
receive a mapping between the source set of data and a model parameter database, wherein the model parameter database comprises a plurality of model parameters for the estimation model;
a processor configured to generate an updated set of model parameters, including by:
determining which model parameters in the model parameter database are mapped to by the mapping; and
updating those model parameters in the model parameter database which are mapped to by the mapping, without updating those model parameters in the model parameter database which are not mapped to by the mapping; and
the model parameter database, which is configured to store the plurality of model parameters.

15. The system of claim 14, wherein:
the interface is further configured to receive one or more parameter space constraints; and
the processor is configured to combine the parameters by using the parameter space constraints.

16. The system of claim 14, wherein the estimation model is selected from a group of a risk model, a conversion model, a default model, and a price sensitivity model.

17. The system of claim 14, wherein the mapping is based on a probabilistic similarity of database attributes and source data attributes.

18. The system of claim 14, wherein the processor is configured to generate, further including by: generating, for at least one model parameter in the updated set of model parameters, a distribution function that includes (1) a range of values for the at least one model parameter and (2) a range of probabilities corresponding to the range of values.

19. The system of claim 18, wherein the processor is configured to generate the distribution function including by: using a distribution function associated with a hyperparameter, wherein:
the distribution function associated with the hyperparameter includes (1) a range of values for the hyperparameter and (2) a range of probabilities corresponding to the range of values for the hyperparameter; and
the distribution function associated with the hyperparameter affects the distribution function generated for the at least one model parameter.

20. The system of claim 18, wherein the distribution function is a combined distribution function and the processor is configured to generate the combined distribution function by: combining (1) a first distribution function, for the at least one model parameter, generated from a first set of data and (2) a second distribution function, for the at least one model parameter, generated from a second set of data which does not overlap with the first set of data.

21. The system of claim 20, wherein at least one of the following is inaccessible when the combined distribution function is generated: the first set of data or the second set of data.

22. A computer program product, the computer program product being embodied in a non-transitory computer readable storage medium and comprising computer instructions for:
receiving a source set of data, wherein the source set of data comprises data representing a plurality of transactions stored in a source transaction database;
receiving an estimation model for modeling data for a transaction;
receiving a mapping between the source set of data and a model parameter database, wherein the model parameter database comprises a plurality of model parameters for the estimation model;
generating an updated set of model parameters, including by:
determining which model parameters in the model parameter database are mapped to by the mapping; and
updating those model parameters in the model parameter database which are mapped to by the mapping, without updating those model parameters in the model parameter database which are not mapped to by the mapping; and storing the updated set of model parameters in the model parameter database.

23. The computer program product of claim 22 further comprising computer instructions for extracting relevant information from the model parameter database using a distance metric function that produces a trade-off of information similarity and time weighting.

24. The computer program product of claim 22 further comprising computer instructions for receiving one or more parameter space constraints, wherein combining the parameters includes using the parameter space constraints.

25. The computer program product of claim 22 further comprising computer instructions for outputting a model by accessing the updated set of model parameters stored in the model parameter database.

26. The computer program product of claim 25, wherein the computer instructions for outputting a model include computer instructions for using a posterior probability.

27. The computer program product of claim 22, wherein the computer instructions for generating further include computer instructions for: generating, for at least one model parameter in the updated set of model parameters, a distribution function that includes (1) a range of values for the at least one model parameter and (2) a range of probabilities corresponding to the range of values.

28. The computer program product of claim 27, wherein the computer instructions for generating the distribution function include computer instructions for using a distribution function associated with a hyperparameter, wherein:

the distribution function associated with the hyperparameter includes (1) a range of values for the hyperparameter and (2) a range of probabilities corresponding to the range of values for the hyperparameter; and the distribution function associated with the hyperparameter affects the distribution function generated for the at least one model parameter.

29. The computer program product of claim 27, wherein the distribution function is a combined distribution function and the computer instructions for generating the combined distribution function include computer instructions for: combining (1) a first distribution function, for the at least one model parameter, generated from a first set of data and (2) a second distribution function, for the at least one model parameter, generated from a second set of data which does not overlap with the first set of data.

30. The computer program product of claim 29, wherein at least one of the following is inaccessible when the combined distribution function is generated: the first set of data or the second set of data.

* * * * *